United States Patent [19]
Mullane

[11] Patent Number: 6,050,997
[45] Date of Patent: Apr. 18, 2000

[54] SPINAL FIXATION SYSTEM

[76] Inventor: Thomas S. Mullane, 1201 River Reach Dr., Suite 512, Ft. Lauderdale, Fla. 33315

[21] Appl. No.: 09/237,175

[22] Filed: Jan. 25, 1999

[51] Int. Cl.[7] ................................................ A61B 17/56
[52] U.S. Cl. ................................................ 606/61; 606/73
[58] Field of Search .................................. 606/61, 72, 73

[56] References Cited

U.S. PATENT DOCUMENTS

| | | |
|---|---|---|
| 4,887,595 | 12/1989 | Heinig et al. . |
| 4,887,596 | 12/1989 | Sherman . |
| 4,946,458 | 8/1990 | Harms et al. . |
| 5,002,542 | 3/1991 | Frigg . |
| 5,129,900 | 7/1992 | Asher et al. . |
| 5,133,717 | 7/1992 | Chopin . |
| 5,569,247 | 10/1996 | Morrison . |
| 5,591,166 | 1/1997 | Bernhardt et al. . |
| 5,716,357 | 2/1998 | Rogozinski . |
| 5,725,528 | 3/1998 | Errico et al. ............................ 606/61 |
| 5,800,435 | 9/1998 | Errico et al. . |

Primary Examiner—Julian W. Woo
Attorney, Agent, or Firm—McHale & Slavin PA

[57] ABSTRACT

An adjustable spinal fixation system comprises a collection of anchoring assemblies attached, via a variety of connectors, to spine-stabilizing rods. The anchoring assemblies include a linking member attached in a ball-and-socket fashion to a bone-engaging member that is adapted to engage a spinal bone of a patient. The linking member joins one of the included connectors to an associated bone-engaging member. The connectors are selectively attached to one of the stabilizing rods. The anchoring assemblies each include a support collar and a retention collet that cooperate to allow adjustment of the bone-engaging member and corresponding connector during surgery. When surgery is complete, a securing nut and locking bolt cooperate with the support collar and retention collet to maintain the relative position of the entire fixation system, preventing unwanted movement between the system components. In one embodiment, the connectors are multi-piece units that may be added or removed without disturbing adjacent connectors.

25 Claims, 9 Drawing Sheets

SPINAL FIXATION SYSTEM

FIELD OF THE INVENTION

This invention is directed to spinal implant systems and, in particular, to a multi-component adjustable implant system capable of maintaining a desired spacial relationship among the bones of a patient's spine.

BACKGROUND OF THE INVENTION

This application provides improvements to the articulating toggle bolt bone screw disclosed in U.S. Pat. No. 5,628,740, issued to Mullane on May 13, 1997. The contents of that patent are hereby incorporated by reference.

For individuals with spinal pathologies, the development of spinal fixation devices represents a major medical breakthrough. Surgically implanted fixation systems are commonly used to correct a variety of back structure problems, including those which occur as a result of trauma or improper development during growth. These fixation systems typically include one or more stabilizing rods aligned in a desired orientation with respect to a patient's spine. Additionally, anchoring screws are inserted into the patient's spinal bones, and a series of connectors is used to rigidly link the rods and anchors.

A variety of designs exist, with each design addressing various aspects of the difficulties that arise when one reshapes an individual's spine to follow a preferred curvature. Unfortunately, known spinal implant systems often correct one set of problems only to create new ones.

Common to spinal implant systems is the necessity for proper anchoring to the bone so as to provide support for the aforementioned components. While bone screws are commonly used for anchoring, they are limited in their positioning due to the design of component pieces. Numerous patents are directed to component design in order to accommodate the bone screw, yet few patents are directed to bone screws that will accommodate existing component design. In many instances the combination of existing component design and bone screw design inhibits application to a particular spinal injury. For example, bone structure of the sacrum is typically soft, and often osteoporotic in the elderly. Perpendicular placement of a bone screw therein may not be possible and placement at an angle thereto may cause undue stress further affecting adjoining bones. Thus, if a common bone screw is employed, the component connector will be of special design.

For this and other reasons, screws located in bone structure typically use a specially designed clamp to attach to a component such as an alignment rod. A problem with specially designed clamps is th at bone structure cannot be determined until the patient's bone is exposed causing the necessity of a large inventory of various sized clamps to be o n hand during surgery, of which the surgeon must search to find the right combination. Even i f a clamp combination is predicted, insertion of the screw may still require angular insertion due to muscle or tender nerve locations. The result is a bone screw which exerts unpredictable forces upon attachment to component connectors. Further, any movement of muscle and other tissue increases the difficulty of the operation and can be a major trauma to a person.

A conventional bone screw consists of a single shaft with a coarse thread at one end for threading into the bone and a machine thread at the other end for coupling to components. Another type of bone screw has a U-shaped top which acts as a saddle for attachment to an alignment rod. If the screw is placed incorrectly for any reason, the rod clamp must be made to accommodate the position.

A number of patents exist which demonstrate the reliance on the saddle type screw support and various designs to accommodate the problem. U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion design for threadingly engaging a Eemi-spherical cup for use with a specially designed alignment rod. The alignment rod having spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are adapted with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900, employ connectors that join the support rods and anchoring screws. The connectors eliminate unwanted relative motion between the rod and the screws, thereby maintaining the patient's spine in a corrected orientation.

Unfortunately, although these so-called "rigid screw" fixation systems can alter the curvature of a patient's spine, they can also be difficult to install. In this type of system, the anchoring screws must be secured in a region that is strong/rigid enough to support the characteristically-large loads typically transferred from the support rods. As a result, the number of suitable anchoring locations is limited. Typically, these screws are anchored into the posterior region of a patient's spinal column or into pedicle bone. With rigid screw systems, installation requires bending a support rod into a path that will not only correct the shape a patient's spine but that will also engage each of the installed anchoring screws. Achieving a proper fit between all of the components while contending with the constraints encountered during surgery is often difficult. In severe cases, a suitable fit may not be achieved and the surgery will be unsuccessful.

Additionally, the nature of the installation process required for rigid screw fixation systems often subjects the system components to pre-loading that unduly stresses the interface between the patient's bone and the employed anchoring screws. With these designs, as a patient moves about during daily life, the system components may become separated from the supporting bone. Corrective surgery to reattach anchoring screws exposes an already-weakened region to additional trauma and presents the risk of additional damage.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths. Unfortunately, some adjustable fixation systems tolerate only limited amounts of relative adjustment between components, operating best when loaded in one of several preferred arrangements. As a result, many adjustable fixation systems provide are suitable for only a few situations.

Additionally, many adjustable fixation systems are prone to post-surgery component loosening. As a patient moves about during day-to-day living, his spine is subjected to a seemingly-endless amount of dynamic loading. Almost all activity requires some form of back motion; over time, this cyclic movement tends to work the components of many adjustable fixation systems loose.

Some adjustable spinal fixation systems include locking mechanisms designed for long-term, post-surgery securement of the system components. Although capable of being locked in place, these systems are often difficult to secure, requiring an excess of tools during the installation process. The need for extra tools, such as those required to shave or crimp key portions of a fixation system, increasing surgical risk by adding complexity and increasing the number of required steps. Although locking-component fixation systems exist, many of them unduly increase the dangers of back implant surgery to an unacceptable level.

Hardware-intensive fasteners are disclosed in U.S. Pat. No. 5,549,608, in which anchoring screws are fitted with wrenching flats that allow an anchoring screw to be attached to a patient's spinal bone with the flats being trimmed away once the screw is in place. Clamping nuts are then used to secure the anchoring screws to included stabilizing rods.

Additionally, many spinal fixation systems do not permit component repairs. If, for example, a threaded portion of a connecting member becomes stripped or cross-threaded, the entire connector must be slid off of the associated stabilizing rod. Often, such removal produces an undesirable "domino-effect," requiring that several connectors be slid off to allow removal of the damaged connector. Such requirements add unnecessary difficulty to an already-complex procedure.

Thus, what is needed is a spinal fixation system that includes the advantages of known devices, while addressing the shortcomings they exhibit. The system should allow component adjustment during installation, thereby enabling satisfactory correction of a wide variety of spinal deformities. The system should also include a component locking mechanism that is simple and reliable. The system should include two-piece connectors that may be mounted along a support rod, in-between previously-secured connectors. The system should also include mounting hardware that secures with a minimum of tools and that allows modular replacement of components damaged during installation.

SUMMARY OF THE INVENTION

The present invention is a spinal fixation system useful in reshaping the spine of a patient. The system is modular, employing a collection of anchoring assemblies that are linked, via various connectors, to strategically-arranged stabilizing rods. The stabilizing rods are shaped and aligned to impart a preferred curvature to a patient's spine.

The anchoring assemblies are multi-piece units characterized by linking members that are joined in a ball-and-socket-type arrangement with a corresponding bone-engaging member. During use, the bone-engaging member is secured to a spinal bone and the linking member is secured to one of the stabilizing rods via a corresponding connector. The bone-engaging member may include coarse, external threads or have a hook-shaped end. Each anchoring assembly also includes a support collar that provides a secure interface between the bone-engaging member and associated connector. Each anchoring assembly also includes a securing nut and a locking bolt that cooperate to prevent unwanted, post-installation motion within the anchoring assembly. The securing nut and locking bolt also prevent unwanted relative motion between the anchoring assembly and associated connector.

The connectors are rigid structures adapted to link an associated anchoring assembly with one of this stabilizing rods. In one embodiment, the connectors are two-piece constructions that allow the connector to engage a stabilizing rod in a sandwich-type arrangement, permitting connector installation and removal that does not disturb adjacent connectors.

The stabilizing rods are rigid members shaped to form a spine-curvature-correcting path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Thus, it is an objective of the present invention to provide a spinal fixation system that permits component adjustment during installation, thereby enabling satisfactory correction of a wide variety of spinal deformities.

It is an additional objective of provide a spinal fixation provide a spinal fixation system that includes a component locking mechanism that is simple and reliable.

It is a further objective of the present invention to provide a spinal fixation system that includes two-piece connectors that may be mounted along, and removed from, a support rod without requiring movement of adjacent connectors.

It is yet another objective of the present invention to provide a spinal fixation system that includes mounting hardware which requires a minimum number of tools.

It is also an objective of the present invention to provide a spinal fixation system that allows modular replacement of damaged components.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

Figure 1:
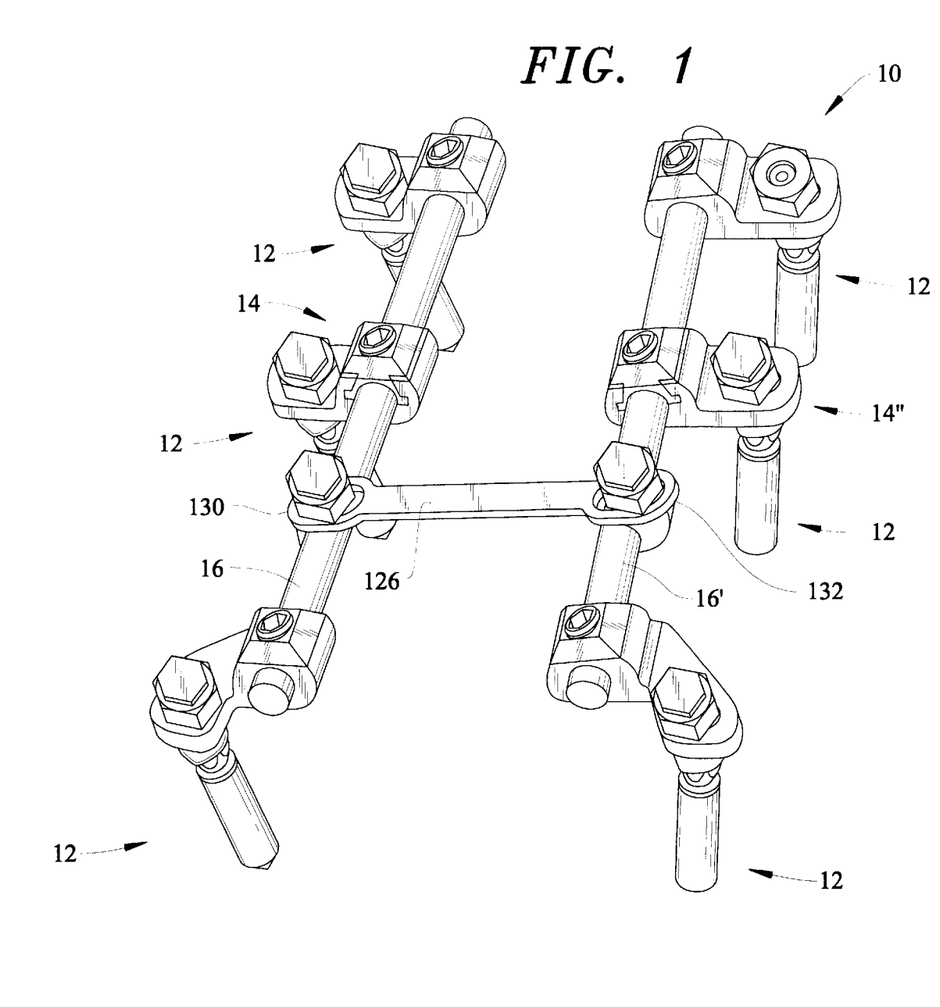
FIG. 1 is a pictorial view of the spinal fixation system of the present invention.

Now with reference to FIG. 1, the spinal fixation system 10 of the present invention is shown. By way of overview, the Fixation System 10 includes a collection of bone-engaging anchoring assemblies 12 that are joined via connectors 14,14' to stabilizing rods 16, 16'. The specifics of the spinal fixation system 10 will now be discussed in more detail.

Figure 2:
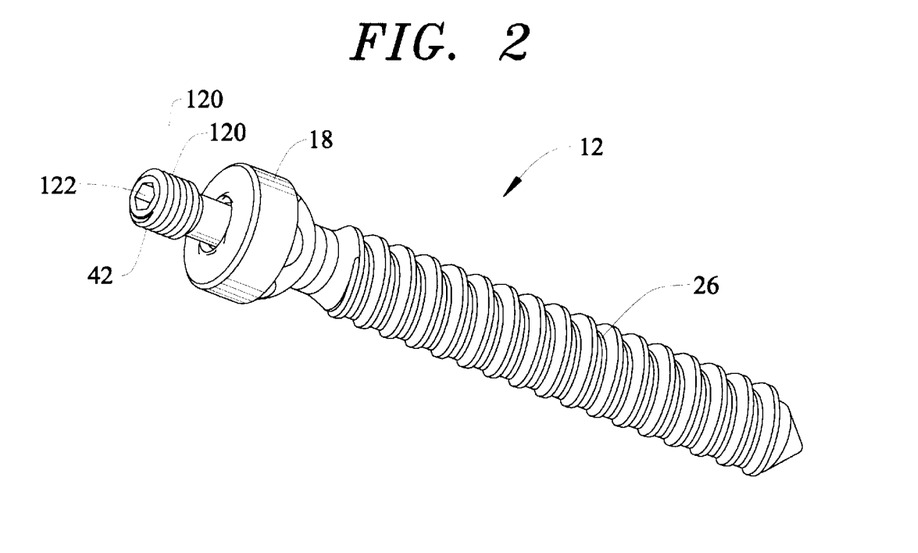
FIG. 2 is a perspective view of an anchoring assembly used in the present spinal fixation system.
Figure 3:
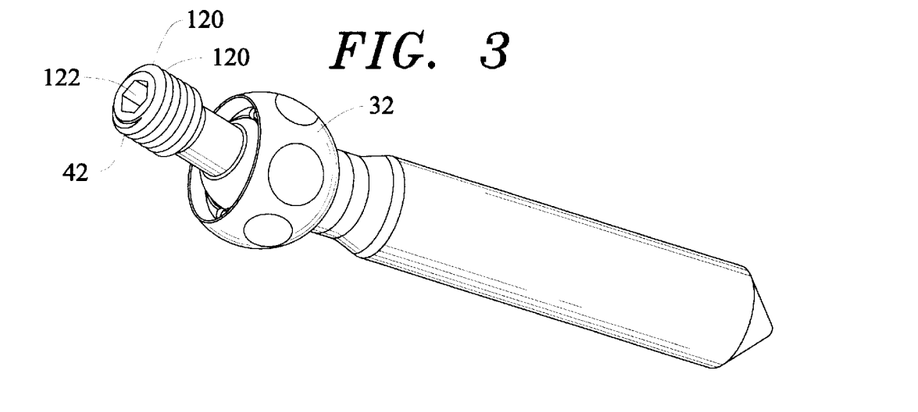
FIG. 3 is a perspective view of an anchoring assembly used in the present spinal fixation system, having a support collar removed.
Figure 3A:
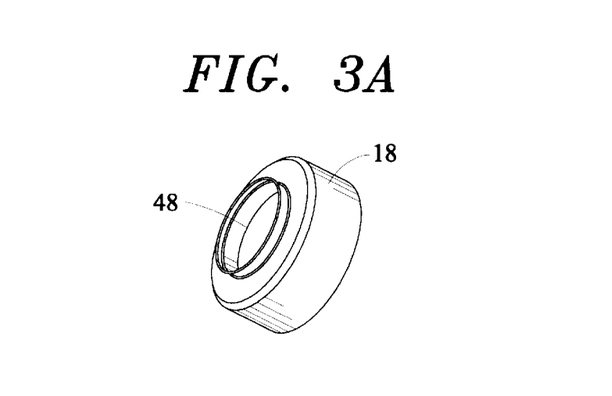
FIG. 3A is a perspective view of a support collar used in the present spinal fixation system.
Figure 4:
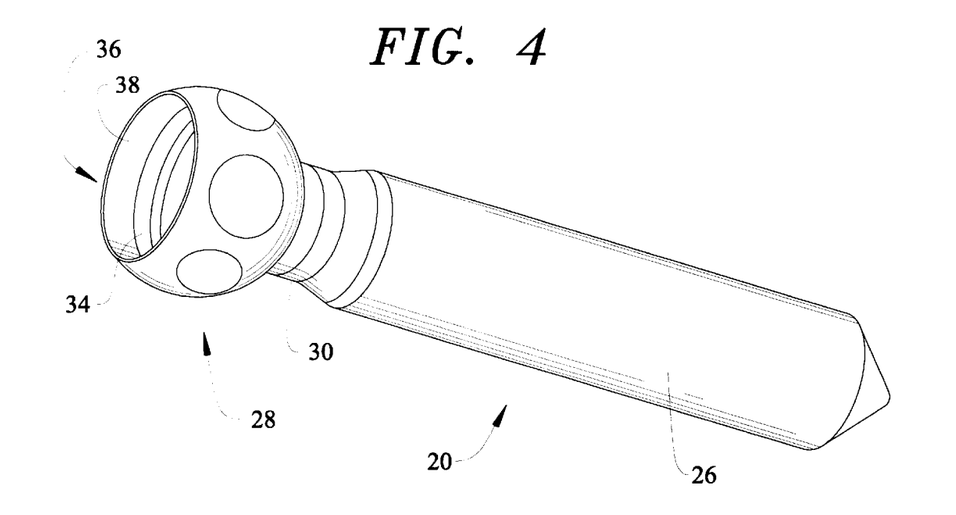
FIG. 4 is a pictorial view of a bone-engaging member from an anchoring assembly of the present invention.

With additional reference to FIG. 2, one of the included anchoring assemblies 12 is shown in an assembled state. FIG. 3 and 3A show the anchoring assembly with an associated support collar 18 removed. In addition to the support collar 18, each anchoring assembly 12 also includes a pedicle screw 20, a toggle bolt 22, and a retention collet 24. As shown in FIG. 4, each pedicle screw 20 includes a threaded end 26 having coarse threads sized to engage bone. Each pedicle screw 20 also includes a ball end 28 spaced apart from the threaded end 26 by a neck portion 30. The exterior 32 of the pedicle screw ball end 28 is preferably contoured for easy grasping. The interior of the pedicle screw ball end 28 forms a retention cavity 34, discussed below. The entrance 36 to the retention cavity 34 is characterized by a securing lip 38 that extends radially into the retention cavity 34.

Figure 4A:
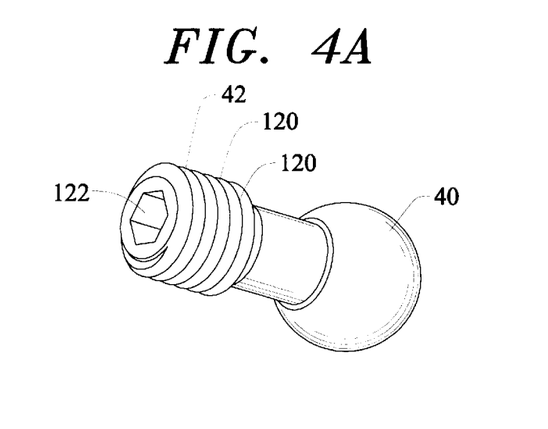
FIG. 4A is a pictorial view of a linking member from an anchoring assembly of the present invention.

Each toggle bolt 22, as shown in FIG. 4A, includes a ball end 40 and an opposite threaded end 42. As seen in FIG. 3, the ball end 40 of the toggle bolt 22 is shaped and sized to fit inside the pedicle screw retention cavity 34. Preferably, the interior of the retention cavity is substantially spherical, thereby matching the spherical contours of the toggle bolt ball end 40.

Figure 4B:
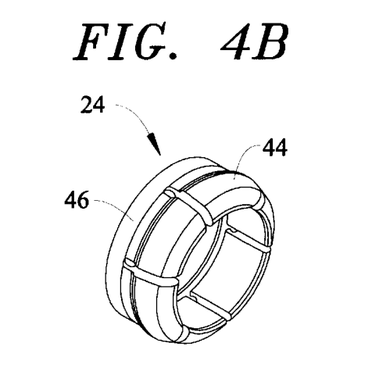
FIG. 4B is a pictorial view of a retention collet of the present invention.

With reference to FIG. 4B, the retention collet 24 includes several wedging flanges 44 that extend from the retention collet main body 46. As seen in FIG. 3, the retention collet 24 is used as a bracing means to secure the ball end 40 of the toggle bolt 22 within the pedicle screw retention cavity 34. More specifically, after the toggle bolt ball end 40 is placed within the pedicle screw retention cavity 34, the retention collet 24 is pushed through the entrance 36 of the retention cavity 34, until the wedging flanges 44 travel past the engagement lip 38, thereby bringing the retention collet main body 46 to rest against the engagement lip.

With this arrangement, the retention collet 24 allows pivotal movement of the toggle bolt 22 within the retention cavity 34, while preventing removal of the toggle bolt therefrom. Once the retention collet 24 and toggle bolt 22 are in place, the threaded end 42 of the toggle bolt is inserted through a passthrough aperture 48 of the support collar 18. This is shown in FIG. 2.

Once the toggle bolt 22 has been passed through the support collar passthrough aperture 48, the support collar 18 comes to rest against the pedicle screw ball end 28. Although several shapes are possible, the interior of the support collar 18 preferably has a spherical contour that marches the exterior 32 of the pedicle screw ball end 28. This arrangement limits the relative motion possible between the support collar 18 and the toggle bolt 22, while allowing the toggle bolt ball end 40 to rotate freely within the pedicle screw retention cavity 34. Although an assembly process has been described above, the anchoring assemblies 12 are typically delivered to the end-user surgeon as a finished unit.

Figure 9:
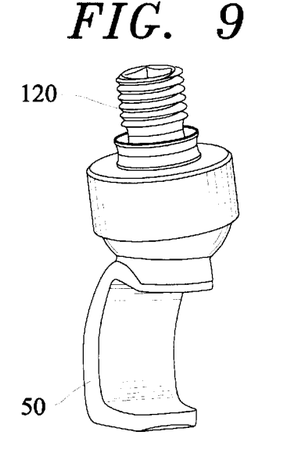
FIG. 9 is a pictorial view of the container of a hook-shaped linking member from an anchoring assembly of the present invention.

In an alternate embodiment, the threaded end 26 of the pedicle screw 20 may be replaced by a hook-shaped section 50. This hook-shaped section 50 allows the anchoring assembly 12 to be used in settings where a screw-like attachment is not appropriate, such as the fixation of bridge connectors 126, discussed below. This hook-shaped section 50 is shown best in FIG. 9.

The spinal fixation system 10 of the present invention includes several types of connectors 14. More specifically, these connectors may take one of several shapes: a right-facing straight connector 52, shown in FIG. 6; a right-facing offset connector 54, shown in FIG. 7; a left-facing offset connector 56, shown in FIG. 8; and a left-facing straight connector 58, shown in FIG. 6A. Each of the various connectors 14 has a preferred use, as shown in FIG. 1. For example, the right-facing connectors 52, 54 are used to secure anchoring assemblies 12 to a right-side-oriented stabilizing rod 16'. The left-facing connectors 56, 58 are, in turn, are used to attach anchoring assemblies 12 to a left-side-oriented stabilizing rod 16.

Figure 5:
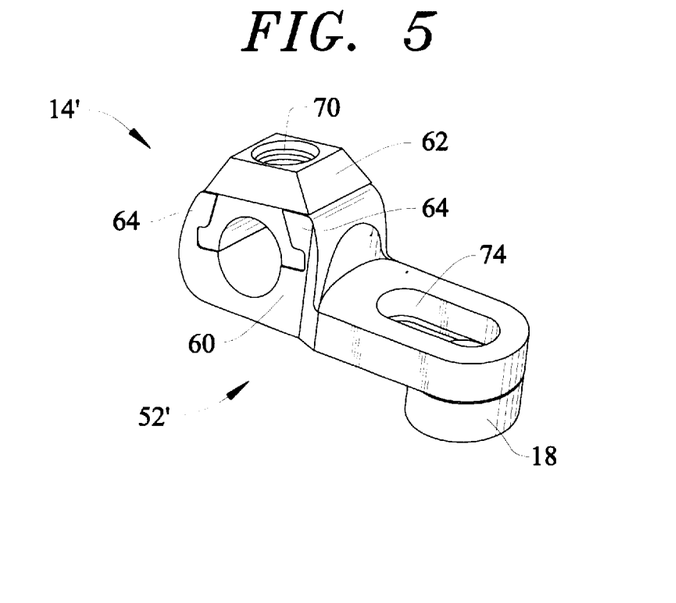
FIG. 5 is a pictorial view of a two-piece connector of the present invention, shown in an assembled state.
Figure 5A:
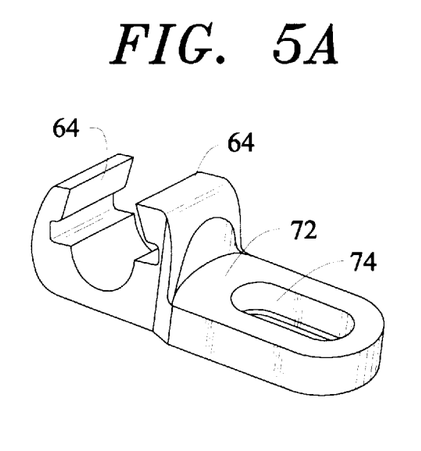
FIG. 5A is a pictorial view of a two-piece connector main body.
Figure 5B:
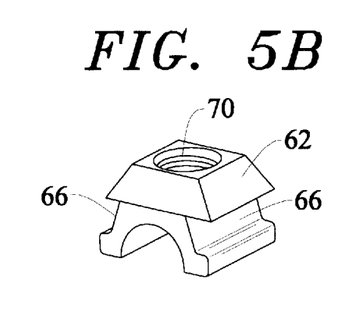
FIG. 5B is a pictorial view of a two-piece connector insertion plug.
Figure 5C:
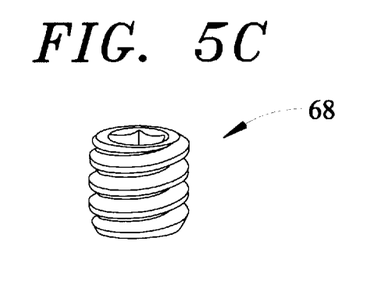
FIG. 5C is a pictorial view of a threaded locking insert of the present invention.

Additionally, each connector 14' may be formed as a two-piece unit. With reference to FIG. 5, a typical right-facing straight connector 52' is shown as a two-piece unit. The two-piece connectors 14' each include a main body 60, shown in FIG. 5A, and a removable locking plug 62 slidably associated therewith. More specifically, the two-piece connector main body 60 has a pair of spaced-apart engagement arms 64. The arms 64 cooperatively fit engagement recesses 66 disposed along opposite sides of the locking plug 62. Because the locking plug 62 of the two-piece connectors 14' is removable, the two-piece connector is very user-friendly. If, for example, the threads within the locking insert aperture 70 become stripped or crossed during insertion of a corresponding threaded locking insert 68, the locking plug 62 may be replaced merely by sliding the locking plug laterally out from between the attachment flanges 72 associated with the connector main body 60. As a result, the entire connector 14' need not be replaced. This reduces possible additional trauma that may otherwise be induced if the entire connector needed to be replaced. A threaded locking insert 68 is shown in FIG. 5C.

The two-piece connector 14' is especially useful as a connector that may be installed once other connectors 14 have already been locked in place. The removable nature of the locking plug allows the connector main body 60 to be attached to a stabilizing rod 16, 16' without the need to slide the connector 14' along the length of the rod. Instead, the main body 60 is secured to an appropriate anchoring assembly 12 and the engagement arms 64 are arranged to straddle an intended attachment location along the rod 16, 16'. The locking plug 62 is then slid into place between the engagement arms 64. As with the one piece connectors 14, the two-piece connectors 14' are locked into place with respect to a stabilizing rod 16, 16' via a threaded locking insert 68, screwed into a locking insert aperture 70 and tightened against the corresponding stabilizing rod 16, 16'.

The two-piece connectors 14' each include an attachment flange 72 extending from the main body 60. The two-piece connector attachment flange 72 includes a passthrough aperture 74 sized to accommodate the threaded end 42 of the toggle bolt 22 associated with a corresponding anchoring assembly 12.

Figure 6:
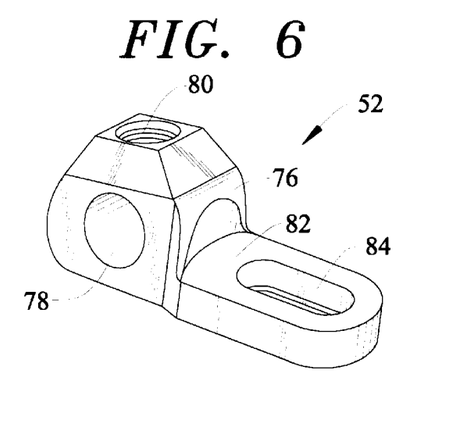
FIG. 6 is a pictorial view of a right-facing straight connector of the present invention.

As seen in FIG. 6, each right-facing straight connector 52 includes a main body 76 characterized by a rod bore 78 and a threaded locking insert aperture 80. An attachment flange 82 extends orthogonally from the main body 76 of each right-facing straight connector 52. The attachment flange 82 includes a passthrough aperture 84. Preferably, the passthrough aperture 84 is oblong and sized to accommodate the threaded end 42 of a toggle bolt 22 associated with a corresponding anchoring assembly 12. As seen in FIG. 1, the rod bore 78 is sized to allow passage there through the right-side stabilizing rod 16'. A threaded locking insert 68 is used to secure the right-facing straight connector 52 to the rod 16'. More specifically, the exterior of the locking insert 68 is threaded to engage the locking insert aperture 80 located within the right-facing straight connector main body 76.

Figure 7:
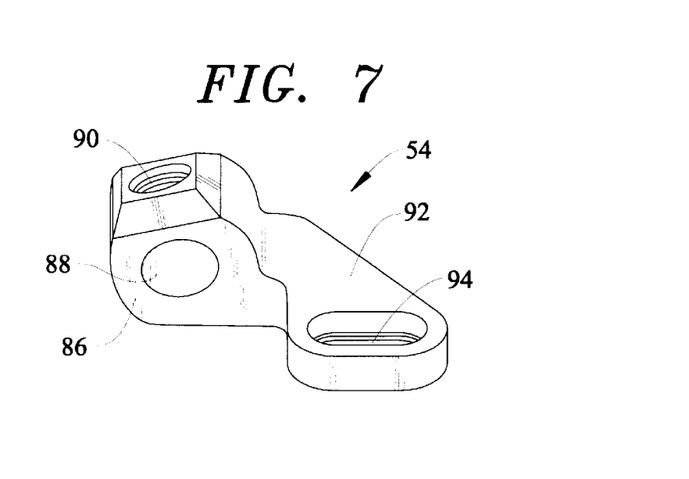
FIG. 7 is a pictorial view of a right-facing offset connector of the present invention.

As seen in FIG. 7, each right-facing offset connector 54 includes a main body 86 characterized by a rod bore 88 and a threaded locking insert aperture 90. An attachment flange 92 extends orthogonally from the main body 86 of each right-facing offset connector 54. The attachment flange 92 includes a passthrough aperture 94. Preferably, the passthrough aperture 94 is oblong and sized to accommodate the thareaded end 42 of a toggle bolt 22 associated with a corresponding anchoring assembly 12. As seen in FIG. 1, the rod bore 88 is sized to allow passage there through the right-side stabilizing rod 16'. A threaded locking insert 78 is used to secure the right-facing offset connector 54 to the rod 16'. More specifically, the exterior of the locking insert 78 is threaded to engage the locking insert aperture 90 located within the right-facing offset connector main body 86.

Figure 8:
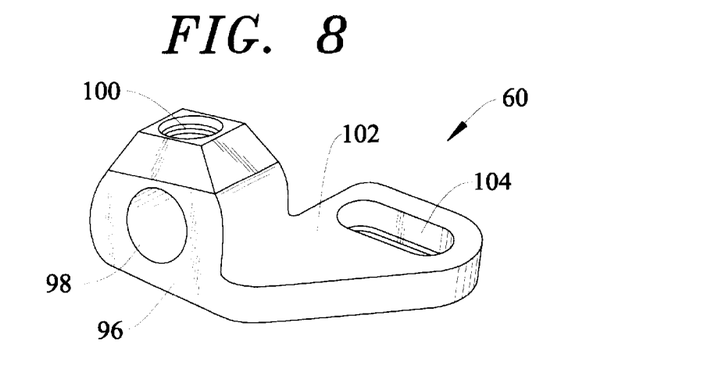
FIG. 8 is a pictorial view of a left-facing offset connector of the present invention.

As seen in FIG. 8, each left-facing offset connector 56 includes a main body 96 characterized by a rod bore 98 and a threaded locking insert aperture 100. An attachment flange 102 extends orthogonally from the main body 96 of each left-facing offset connector 56. The attachment flange 102 includes a passthrough aperture 104. Preferably, the passthrough aperture 104 is oblong and sized to accommodate the threaded end 42 of a toggle bolt 22 associated with a corresponding anchoring assembly 12. As seen in FIG. 1, the rod bore 98 is sized to allow passage there through the left-side stabilizing rod 16. A threaded locking insert 68 is used to secure the left-facing offset connector 56 to the rod 16. More specifically, the exterior of the locking insert 68 is threaded to engage the locking insert aperture 100 located within the left-facing offset connector main body 96.

Figure 6A:
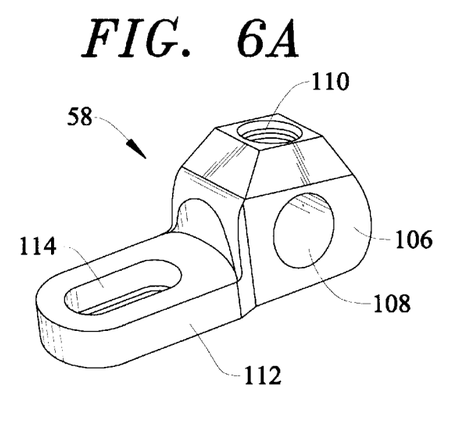
FIG. 6A is a pictorial view of the container of a left-facing straight connector of the present invention.

As seen in FIG. 6A, each left-facing straight connector 58 includes a main body 106 characterized by a rod bore 108 and a threaded locking insert aperture 110. An attachment flange 112 extends orthogonally from the main body 106 of each left-facing straight connector 58. The attachment flange 112 includes a passthrough aperture 114. Preferably, the passthrough aperture 114 is oblong and sized to accommodate the threaded end 42 of a toggle bolt 22 associated with a corresponding anchoring assembly 12. As seen in FIG. 1, the rod bore 108 is sized to allow passage there through the left-side stabilizing rod 16. A threaded locking insert 68 is used to secure the left-facing straight connector 56 to the rod 16. more specifically, the exterior of the locking insert 68 is threaded to engage the locking insert aperture 110 located within the left-facing straight connector main body 96.

Each of the one-piece connectors 14 and two-piece connectors 14' is joined to one of the anchoring assemblies 12 a securing nut 116 and a locking bolt 118. With reference FIG. 4A, the toggle bolt threaded end 42 has exterior threads 120 and a threaded interior bore or locking bolt cavity 122. The exterior threads 120 follow a right handed thread pattern and correspond with the threads of the securing nut 116. However, the threaded interior bore 122 of the toggle bolt threaded end 42 has threads that follow a left handed pattern. The locking bolt 118, which has a left-handed thread pattern as well, screws into the threaded bolt cavity 122.

With this arrangement, an anchoring assembly 12 may be joined, for example, to a right-facing straight connector 52 as follows: A corresponding toggle bolt threaded end 42 is inserted through the passthrough aperture 84 of the connector attachment flange 82. The toggle bolt 22 is held in place by tightening a securing nut 116 downward along the toggle bolt exterior threads 120.

With additional reference to FIG. 3, the threaded interior bore 122 of the toggle bolt threaded end 42 has a hexagonal cross section. This allows the insertion of an allen wrench, not shown, into the interior bore 122 to prevent relative motion between the spherical ball end 40 of the toggle bolts 22 and the spherical retention cavity 34 of the pedicle screw 20. The inserted allen wrench thereby prevents unwanted spinning of the toggle bolt 22 within the retention cavity 34 while the securing nut 116 is tightened onto the exterior threads 120.

Tightening the securing nut 116 forces the toggle bolt threaded end 42 to travel longitudinally through the passthrough aperture 84 and also causes the toggle bolt ball end 40 to be forced against the retention collet wedging flanges 44. Further tightening of the securing nut 116 forms a substantially rigid fit between the toggle bolt 22 and the pedicle screw 20. With the securing nut 116 tightened appropriately, the toggle bolt threaded end 42 is locked in place with regard to the right-facing straight connector attachment flange 82, and the toggle bolt ball end 40 is locked in place within the pedicle screw retention cavity 34. In this state, the retention collet wedging flanges 44 are sandwiched between the exterior of the toggle bolt ball end 40 and the interior of the retention cavity 34. Since the retention collet 34 is locked within the retention cavity 34 by the retention cavity engagement lip 38, relative motion between the toggle bolt ball end and the pedicle screw 20 is prevented once the toggle bolt threaded end 42 is locked in place by the tightened securing nut 116. This results in a rigid link between the right-facing straight connector 52 and the anchoring assembly 12.

Although the above description refers to joining an anchoring assembly 12 specifically to a right-facing straight connector 52, each of the one-piece connectors 14 and two-piece connectors 14' may be attached to an anchoring assembly in a similar manner. That is, right-facing offset connectors 54 are attached by inserting a toggle bolt threaded end 42 through the associated passthrough aperture 94; left-facing offset connectors 56 are joined with an anchoring assembly by inserting a toggle bolt threaded end through an associated passthrough aperture 104; and left-facing straight connectors 58 are attached to anchoring assemblies by inserting a toggle bolt threaded end through an associated passthrough aperture 114. In each case, the exterior threads 120 of the inserted toggle bolt threaded end 42 are held in place by a tightened securing nut 116, as described previously.

To prevent unwanted loosening of a connector 14, 14' and anchoring assembly 12 union, a locking bolt 118 is inserted into the threaded interior bore 122 of the toggle bolt 22 corresponding to each anchoring assembly that has been secured in place. As mentioned above, each locking bolt 118 has a left-handed thread pattern, thereby matching the left-handed thread pattern of each toggle bolt threaded interior bore 122. The locking bolt 118 is screwed into an associated toggle bolt threaded interior bore 122 until the locking bolt head plate 124 comes to rest against the securing nut 116 that holds the corresponding anchoring assembly 12 in places with respect to the associated connector 14, 14'. Incorporating this locking bolt 118 ensures that anchoring assemblies 12 and connectors 14, 14' stay locked in place, thereby preventing unwanted relative motion within the spinal fixation system 10.

Figure 14:
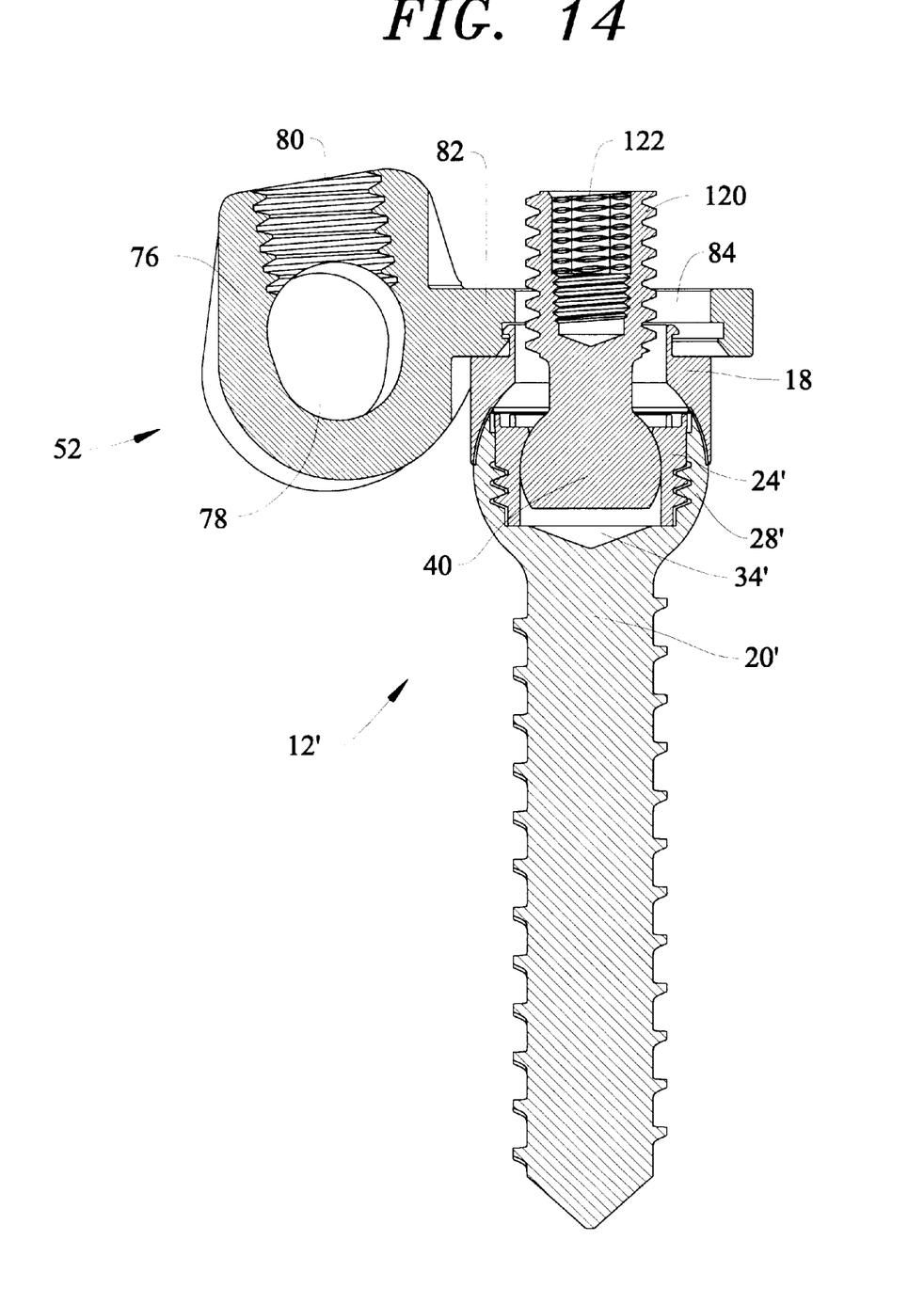
FIG. 14 is a pictorial view of an alternate embodiment of an anchoring assembly and connector of the present invention.

Now with reference to FIG. 14, an alternate embodiment of an anchoring assembly 12' is shown secured to a right-facing straight connector 52. In this embodiment, a alternate retention collet 24' is used to secure the toggle bolt ball end 40 within a securing cavity 34' disposed within the ball end 28 of an associated pedicle screw 20'. Relative position between the pedicle screw 20 and the connector 52 is maintained by an associated support collar 18. The support collar 18 is disposed between the pedicle screw ball end 28' and the attachment flange 82 of the connector 52.

Figure 15:
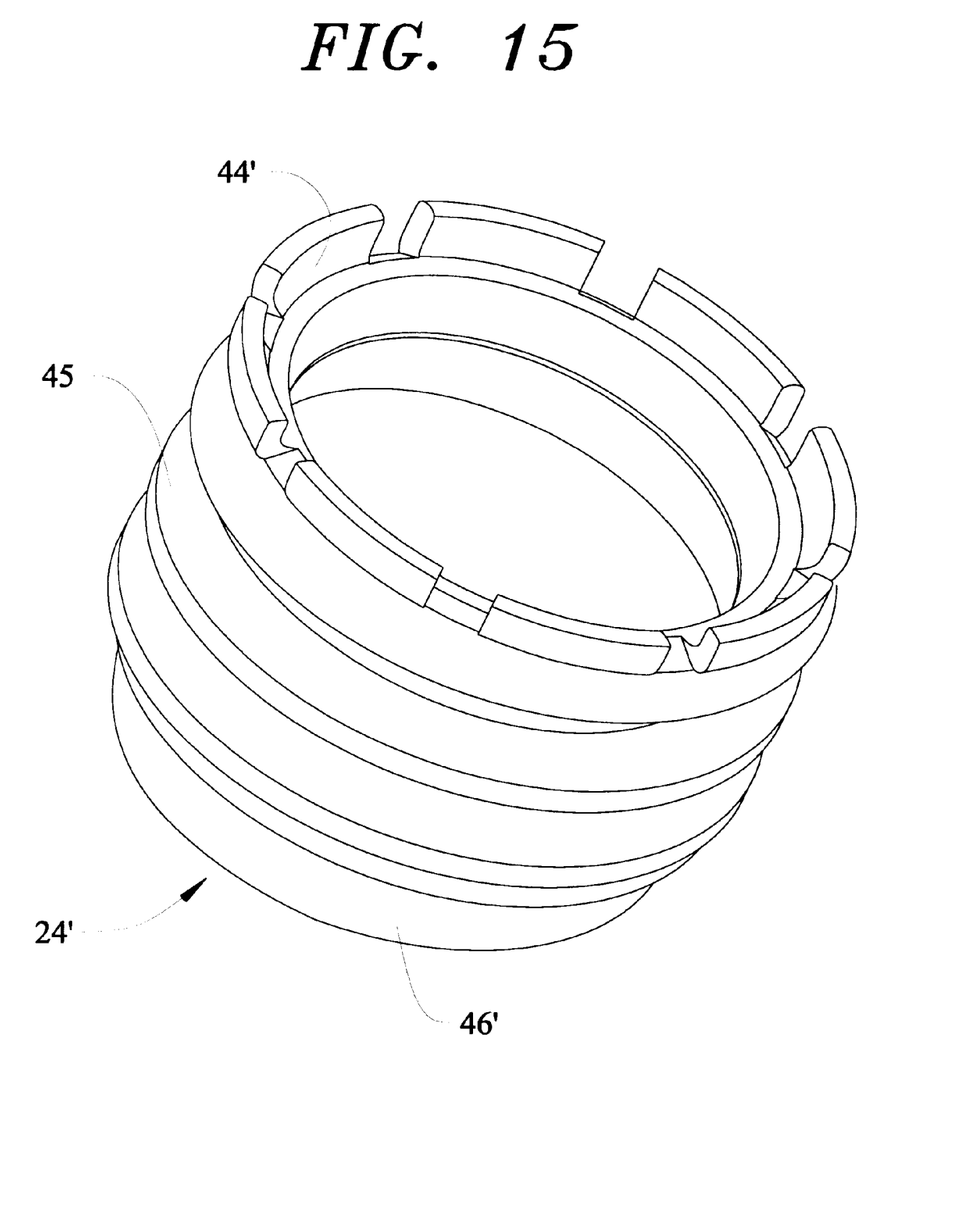
FIG. 15 is a close-up view of an alternate embodiment of a retention collet of the present invention.
Figure 16:
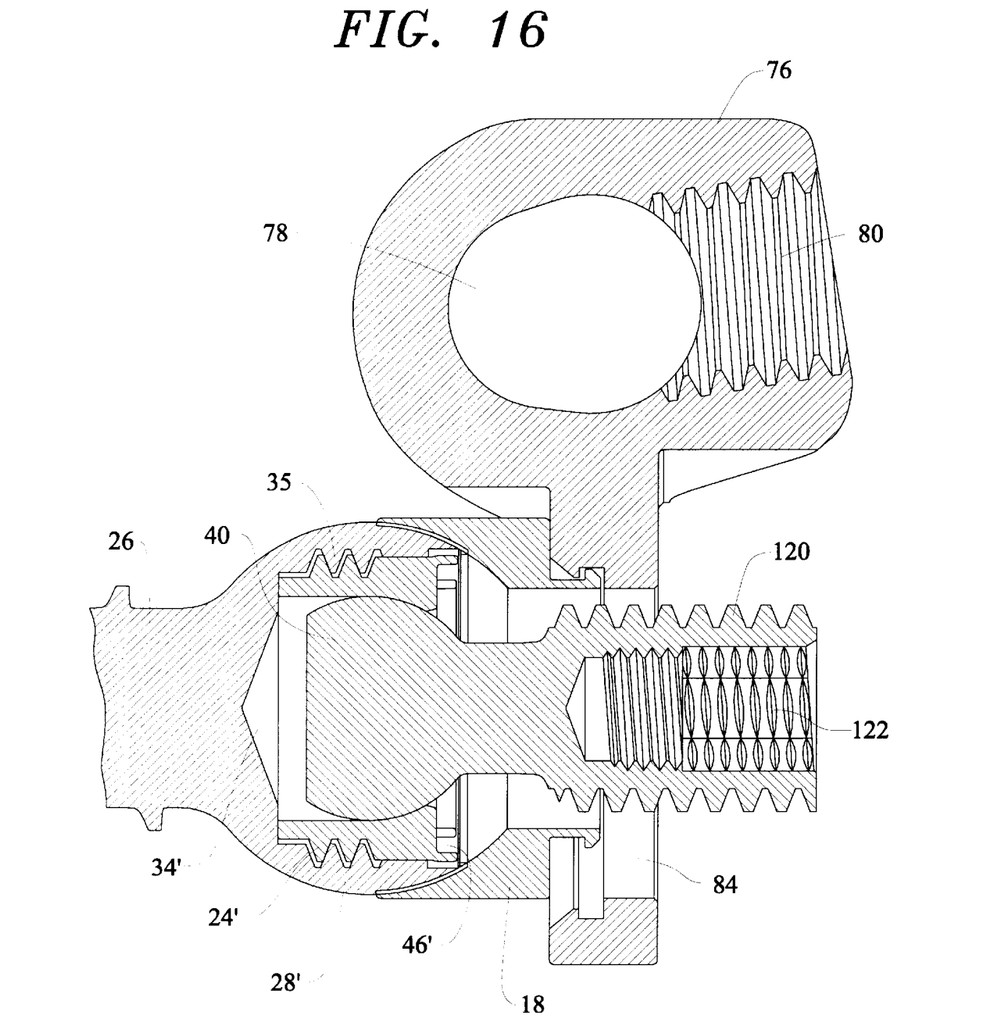
FIG. 16 is a close-up view of the alternate anchoring assembly and connector shown in FIG. 14.

With reference to FIG. 15, a close-up view of an alternate embodiment of the retention collet 24' is shown. The exterior surface of the collet 24' is characterized by external threads 45. With additional reference to FIG. 16, the collet external threads 45 are shaped to engage internal threads 35 disposed within the retention cavity 34. Additionally, the retention collet 24' includes wedging flanges 44' shaped and sized to engage the exterior surface of an associated toggle bolt ball end 40.

The spinal fixation system 10 is preferably formed from rigid, biocompatible materials. One such preferred material is titanium; however, other materials may be used as well.

Figure 10:
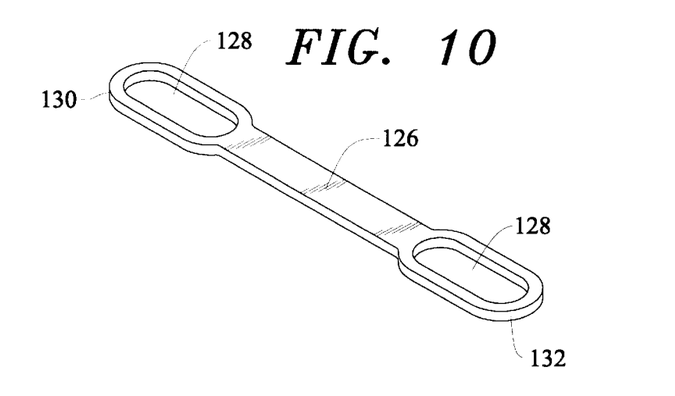
FIG. 10 is a pictorial view of a bridge connector of the present invention.
Figure 11:
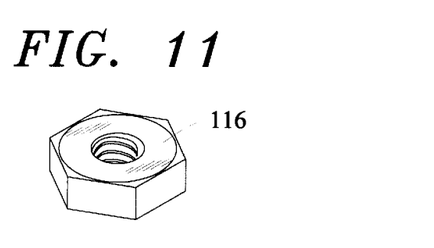
FIG. 11 is a pictorial view of a securing nut of the present invention.
Figure 12:
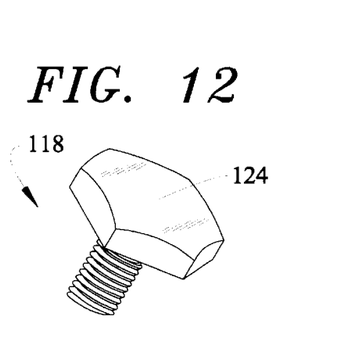
FIG. 12 is a pictorial view of a locking bolt of the present invention.
Figure 13:
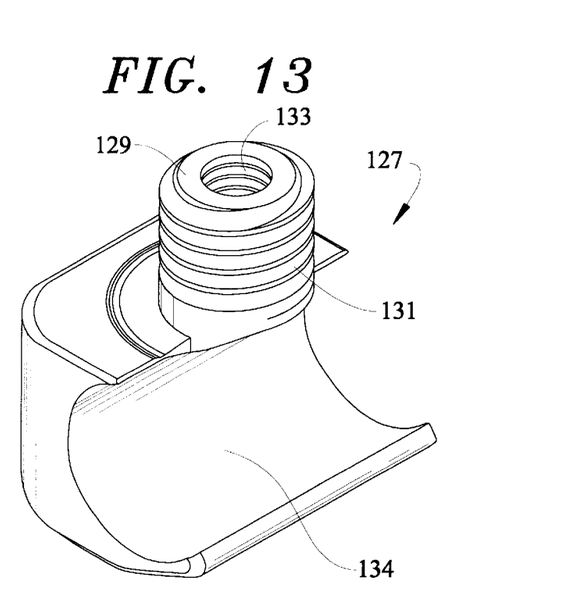
FIG. 13 is a pictorial view of a rod-engaging threaded locking insert of the present invention.

The bridge connector 126 shown in FIG. 10 is used to provide additional support along the stabilizing rods 16, 16', as shown in FIG. 1. With reference to FIG. 10, the bridge connector 126 includes passthrough apertures 128, located at opposite ends 130,132 of the connector. Typically, the bridge connector 126 is held in place with an anchoring assembly 12 that includes a hook-shaped section 50, shown in FIG. 9. Each bridge connector end 130, 132 is secured to a corresponding stabilizing rod 16, 16' by inserting the threaded end 42 of a toggle bolt 22 through the bridge connector passthrough apertures 128. The toggle bolt 22 is held in place with a securing nut 116 and a locking bolt 118. This prevents unwanted motion of the bridge connector 126 and ensures proper spacing between the stabilizing rods 16, 16'. The bridge connectors 126, themselves, are attached to stabilizing rods 16,16' via a bridge attachment member 127, shown in FIG. 13. Each bridge attachment member 127 includes an engagement neck 129 sized for insertion into a bridge connector passthrough aperture 129. The engagement neck 129 includes external threads 131 and internal threads 133, with the threads pitched to accommodate the previously described securing nuts 116 and locking bolts 118. Each bridge attachment member 127 is further characterized by a rod engagement cavity 134 shaped to engage the outer contours of a corresponding stabilizing rod 16,16'.

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

What is claimed is:

1. An anchoring assembly comprising:
   a linking member having a threaded first end and a substantially-spherical second end;
   a bone-engaging member having a first end adapted to engage said bone and a second end comprising a retention cavity constructed and arranged to engage said linking member second end, said retention cavity having a substantially-spherical exterior surface;
   a bracing means for selectively maintaining said linking member second end in a chosen orientation within said retention cavity;
   a support collar adapted for placement against said bone-engaging member second end, said collar having a contoured surface sized and shaped to adjustably engage said exterior surface of said bone-engaging member second end;
   whereby said bracing means selectively prevents relative motion between said linking member and said bone-engaging member.

2. The anchoring assembly of claim 1, wherein said bracing means includes:
   a securing nut mounted on said threaded first end of said linking member;
   a retention collet mounted within an entrance to said retention cavity, said retention collet comprising a main body having a substantially-circular cross section and a plurality of wedging flanges that extend from said main body, the diameter of said circular cross section being smaller than the diameter of said linking member spherical second end, whereby said retention collet prevents removal of said linking member second end from within said retention cavity, and whereby tightening said securing nut draws said linking member second end against said wedging flanges, thereby preventing motion of said linking member with respect to said bone-engaging member.

3. The anchoring assembly of claim 2, wherein said anchoring assembly is adapted for use with at least one connector adapted to selectively engage at least one stabilizing element, said anchoring assembly further including:
   a locking means for attaching said linking member second end to said connector, said locking means including a securing nut adapted to engage an exterior of said linking member second threaded first end; and a locking bolt adapted to engage internal threads located within a bolt cavity longitudinally disposed within said linking member second end;
   whereby said securing nut maintains said linking member second end in place when said second end extends through a passthrough aperture, of said connection and whereby a locking bolt prevents unwanted relative motion between said securing nut and said linking member.

4. The anchoring assembly of claim 3, wherein:
   said exterior of said linking member first end forms a helix having a first pitch and said internal threads within said bolt cavity form a helix having a second pitch, said second pitch being opposite said first pitch.

5. A spinal fixation system comprising:
   at least one stabilizing rod;
   a plurality of connectors adapted to selectively engage said at least one stabilizing rod;
   a plurality of anchoring assemblies each adapted to secure one of said connectors to a spinal bone of an individual, each of said anchoring assemblies including a linking member having a threaded first end and a substantially-spherical second end, said threaded first end being sized to engage one of said connectors; and a bone-engaging member having a first end adapted to engage said bone and a second end comprising a retention cavity constructed and arranged to engage said linking member second end, said retention cavity having a substantially-spherical exterior surface;
   a locking means for attaching said linking member second end to one of said connectors;
   a bracing means for selectively maintaining said linking member second end in a chosen orientation within said retention cavity;
   a support collar adapted for placement between said bone-engaging member second end and one of said connectors; said collar having a contoured first surface sized and shaped to adjustably engage said exterior surface of said bone-engaging member second end, and a second surface sized and shaped to abut one of said connectors;
   whereby said support collar provides a force distributing interface that transfers loads uniformly between said anchoring assembly and one of said connectors regardless of orientation of said linking member relative to said bone-engaging member, thereby allowing adjustable securement of said anchoring assembly to one of said connectors; and whereby said bracing means prevents relative motion between said anchoring assembly and said corresponding connector once said anchoring assembly and said corresponding connector have been arranged in a spinal-curve-correcting orientation.

6. The spinal fixation system of claim 5, wherein each of said connectors includes:
   a rod-engaging bore adapted to accept one of said stabilizing rods;
   a passthrough aperture oriented transverse to said rod-engaging bore, said passthrough aperture being sized to accommodate said linking member first end; and a threaded insert adjustably disposed within a locking insert aperture spanning between an exterior surface of said connector to said rod-engaging bore, whereby said threaded insert adjustably locks said connector to one of said stabilizing rods inserted through said rod-engaging bore.

7. The spinal fixation system of claim 6, wherein at least one of said connectors is a two-piece assembly comprising a main body and a locking plug removably attached thereto, said locking insert aperture being disposed within said locking plug, and said passthrough aperture being disposed with said main body.

8. The spinal fixation system of claim 5, wherein said locking means includes:
   a securing nut adapted to engage an exterior of said linking member threaded first end; and
   a locking bolt adapted to engage internal threads located within a bolt cavity longitudinally disposed within said linking member second end;
   whereby said securing nut maintains said linking member second end in place when said second end extends through said passthrough aperture, and whereby said locking bolt prevents unwanted relative motion between said securing nut and said linking member.

9. The spinal fixation system of claim 8, wherein said exterior of said linking member first end forms a helix having a first pitch and said internal threads within said bolt cavity form a helix having a second pitch, said second pitch being opposite said first pitch.

10. The spinal fixation system of claim 8, wherein said bolt cavity of said linking member second end has a substantially-hexagonal cross section.

11. The spinal fixation system of claim 8, wherein said bracing means includes a retention collet mounted within an entrance to said retention cavity, said retention collet comprising a main body having an essentially-circular cross section and a plurality of wedging flanges that extend from said main body, the diameter of said circular cross section being smaller than the diameter of said linking member spherical second end, whereby said retention collet prevents removal of said linking member second end from within said retention cavity, and whereby tightening said securing nut draws said linking member second end against said wedging flanges, thereby preventing motion of said linking member with respect to said bone-engaging member.

12. The spinal fixation system of claim 5, wherein said bone-engaging member is a screw having threads adapted to engage a spinal bone of said patient.

13. The spinal fixation system of claim 5, wherein said bone-engaging member is hooked shaped.

14. A spinal fixation system for use with at least one spine stabilizing rods, said system comprising:
   a plurality of connectors adapted to selectively engage said at least one stabilizing rod;
   a plurality of anchoring assemblies each adapted to secure one of said connectors to a spinal bone of an individual, each of said anchoring assemblies including a linking member having a threaded first end and a substantially-spherical second end, said threaded first end being sized to engage one of said connectors; and a bone-engaging member having a first end adapted to engage said bone and a second end comprising a retention cavity constructed and arranged to engage said linking member second end, said retention cavity having a substantially-spherical exterior surface;
   a locking means for attaching said linking member second end to one of said connectors;
   a bracing means for selectively maintaining said linking member second end in a chosen orientation within said retention cavity;
   a support collar adapted for placement between said bone-engaging member second end and one of said connectors; said collar having a contoured first surface sized and shaped to adjustably engage said exterior surface of said bone-engaging member second end, and a second surface sized and shaped to abut one of said connectors;
   whereby said support collar provides a force distributing interface that transfers loads uniformly between said anchoring assembly and one of said connectors regardless of orientation of said linking member relative to said bone-engaging member, thereby allowing adjustable securement of said anchoring assembly to one of said connectors; and whereby said bracing means prevents relative motion between said anchoring assembly and said corresponding connector once said anchoring assembly and said corresponding connector have been arranged in a spinal-curve-correcting orientation.

15. The spinal fixation system of claim 14, wherein each of said connectors includes:
   a rod-engaging bore adapted to accept one of said stabilizing rods;
   a passthrough aperture oriented transverse to said rod-engaging bore, said passthrough aperture being sized to accommodate said linking member first end; and a threaded insert adjustably disposed within a locking insert aperture spanning between an exterior surface of said connector to said rod-engaging bore, whereby said threaded insert adjustably locks said connector to one of said stabilizing rods inserted through said rod-engaging bore.

16. The spinal fixation system of claim 15, wherein at least one of said connectors is a two-piece assembly comprising a main body and a locking plug removably attached thereto, said locking insert aperture being disposed within said locking plug, and said passthrough aperture being disposed with said main body.

17. The spinal fixation system of claim 14, wherein said locking means includes:
   a securing nut adapted to engage an exterior of said linking member threaded first end; and
   a locking bolt adapted to engage internal threads located within a bolt cavity longitudinally disposed within said linking member second end;
   whereby said securing nut maintains said linking member second end in place when said second end extends through said passthrough aperture, and whereby said locking bolt prevents unwanted relative motion between said securing nut and said linking member.

18. The spinal fixation system of claim 17, wherein said exterior of said linking member first end forms a helix having a first pitch and said internal threads within said bolt cavity form a helix having a second pitch, said second pitch being opposite said first pitch.

19. The spinal fixation system of claim 17, wherein said bolt cavity of said linking member second end has a substantially-hexagonal cross section.

20. The spinal fixation system of claim 17, wherein said bracing means includes a retention collet mounted within an entrance to said retention cavity, said retention collet comprising a main body having an essentially-circular cross section and a plurality of wedging flanges that extend from said main body, the diameter of said circular cross section being smaller than the diameter of said linking member spherical second end, whereby said retention collet prevents removal of said linking member second end from within said retention cavity, and whereby tightening said securing nut draws said linking member second end against said wedging flanges, thereby preventing motion of said linking member with respect to said bone-engaging member.

21. An anchoring assembly for use with a spinal fixation system, said spinal fixation system including at least one spine stabilizing rod and at least one connector adapted to selectively engage said at least one stabilizing rod, said anchoring assembly comprising:

a linking member having a threaded first end and a substantially-spherical second end, said threaded first end being sized to engage said connector;

a bone-engaging member having a first end adapted to engage said bone and a second end comprising a retention cavity constructed and arranged to engage said linking member second end, said retention cavity having a substantially-spherical exterior surface;

a locking means for attaching said linking member second end to said connector;

a bracing means for selectively maintaining said linking member second end in a chosen orientation within said retention cavity;

a support collar adapted for placement between said bone-engaging member second end and said connector, said collar having a contoured surface sized and shaped to adjustably engage said exterior surface of said bone-engaging member second end, and a second surface sized and shaped to abut said connector;

whereby said support collar provides a force distributing interface that transfers loads uniformly between said anchoring assembly and said connector regardless of orientation of said linking member relative to said bone-engaging member, thereby allowing adjustable securement of said anchoring assembly to said connector; and whereby said bracing means prevents relative motion between said anchoring assembly and said connector once said anchoring assembly and said connector have been arranged in a spinal-curve-correcting orientation.

22. The anchoring assembly of claim 21, wherein said locking means includes:

a securing nut adapted to engage an exterior of said linking member threaded first end; and a locking bolt adapted to engage internal threads located within a bolt cavity longitudinally disposed within said linking member second end;

whereby said securing nut maintains said linking member second end in place when said second end extends through said passthrough aperture, and whereby said locking bolt prevents unwanted relative motion between said securing nut and said linking member.

23. The anchoring assembly of claim 22, wherein said bracing means includes:

a retention collet mounted within an entrance to said retention cavity, said retention collet being comprising a main body having a substantially-circular cross section and a plurality of wedging flanges that extend from said main body, the diameter of said circular cross section being smaller than the diameter of said linking member spherical second end, whereby said retention collet prevents removal of said linking member second end from within said retention cavity, and whereby tightening said securing nut draws said linking member second end against said wedging flanges, thereby preventing motion of said linking member with respect to said bone-engaging member.

24. The anchoring assembly of claim 22, wherein:

said exterior of said linking member first end forms a helix having a first pitch and said internal threads within said bolt cavity form a helix having a second pitch, said second pitch being opposite said first pitch.

25. The anchoring assembly of claim 22, further including a plurality of said locking means having a plurality of securing nuts and locking bolts;

a bridge connector adapted to span between two of said stabilizing rods; and a plurality of connector attachment members each adapted to selectively secure one end of said bridge connector to a corresponding one of said rods; said connector attachment members having an engagement neck adapted to engage one of said securing nuts and one of said locking bolts; said bridge connectors having a rod engaging cavity adapted to engage the exterior of a corresponding one of said rods;

whereby said bridge connectors and said connector attachment members cooperatively maintain said rods in a spaced apart relationship, and whereby said securing nuts and said locking bolts cooperatively maintain said connector attachment members in a selectively fixed relationship.

* * * * *